United States Patent
Lin et al.

(10) Patent No.: US 7,258,734 B2
(45) Date of Patent: Aug. 21, 2007

(54) INJECTABLE CALCIUM PHOSPHATE CEMENTS AND THE PREPARATION AND USE THEREOF

(75) Inventors: Jiin-Huey Chern Lin, Winnetka, IL (US); Chien-Ping Ju, Carbondale, IL (US); Wen-Cheng Chen, Tainan Hsien (TW)

(73) Assignee: Calcitec, Inc., Austin, TX (US)

( * ) Notice: Subject to any disclaimer, the term of this patent is extended or adjusted under 35 U.S.C. 154(b) by 0 days.

(21) Appl. No.: 11/129,227

(22) Filed: May 13, 2005

(65) Prior Publication Data

US 2005/0268819 A1  Dec. 8, 2005

Related U.S. Application Data

(63) Continuation of application No. 10/414,582, filed on Apr. 16, 2003, which is a continuation-in-part of application No. 09/615,384, filed on Jul. 13, 2000, now abandoned, which is a continuation-in-part of application No. 09/351,912, filed on Jul. 14, 1999, now Pat. No. 6,379,453.

(51) Int. Cl.
C04B 28/34 (2006.01)
(52) U.S. Cl. .................. 106/690; 428/403; 427/215
(58) Field of Classification Search ........... 106/690, 106/691, 35
See application file for complete search history.

(56) References Cited

U.S. PATENT DOCUMENTS 3,679,360 A   7/1972   Rubin et al.
4,371,484 A   2/1983   Inukai et al.
4,481,175 A   11/1984  Iino et al.
4,518,430 A   5/1985   Brown et al.
4,553,272 A   11/1985  Mears
4,612,053 A   9/1986   Brown et al.
4,623,553 A   11/1986  Ries et al.
RE33,161 E    2/1990   Brown et al.
RE33,221 E    5/1990   Brown et al.
4,959,104 A   9/1990   Iino et al.
5,017,518 A   5/1991   Hirayama et al.

(Continued)

FOREIGN PATENT DOCUMENTS

JP   06-228011   8/1994

(Continued)

OTHER PUBLICATIONS

Sugawara et al., "Calcium Phosphate Cement: An In Vitro study of Dentin Hypersensitivity", The Journal of the Japanese Society for Dental Materials and Devices, 1989, vol. 8, pp. 282-294.

(Continued)

*Primary Examiner*—C. Melissa Koslow
(74) *Attorney, Agent, or Firm*—Meyertons, Hood, Kivlin, Kowert & Goetzel, P.C.; Eric B. Meyertons

(57) ABSTRACT

A calcium phosphate cement suitable for use in dental and bone prosthesis is disclosed, which include calcium phosphate particles having a diameter of 0.05 to 100 microns, wherein said calcium phosphate particles on their surfaces have whiskers or fine crystals having a width ranging from 1 to 100 nm and a length ranging from 1 to 1000 nm.

11 Claims, 11 Drawing Sheets

U.S. PATENT DOCUMENTS

| | | |
|---|---|---|
| 5,053,212 A | 10/1991 | Constantz et al. |
| 5,092,888 A | 3/1992 | Iwamoto et al. |
| 5,149,368 A | 9/1992 | Liu et al. |
| 5,152,791 A | 10/1992 | Hakamatsuka et al. |
| 5,164,187 A | 11/1992 | Constantz et al. |
| 5,180,426 A | 1/1993 | Sumita |
| 5,218,035 A | 6/1993 | Liu |
| 5,262,166 A | 11/1993 | Liu et al. |
| 5,336,264 A | 8/1994 | Constanz et al. |
| 5,338,356 A | 8/1994 | Hirano et al. |
| 5,342,441 A | 8/1994 | Mandai et al. |
| 5,409,982 A | 4/1995 | Imura et al. |
| 5,476,647 A | 12/1995 | Chow et al. |
| 5,492,768 A | 2/1996 | Okimatsu et al. |
| 5,496,399 A * | 3/1996 | Ison et al. .................... 106/35 |
| 5,503,164 A | 4/1996 | Friedman |
| 5,522,893 A | 6/1996 | Chow et al. |
| 5,525,148 A | 6/1996 | Chow et al. |
| 5,536,575 A | 7/1996 | Imura et al. |
| 5,542,973 A | 8/1996 | Chow et al. |
| 5,545,254 A | 8/1996 | Chow et al. |
| 5,550,172 A | 8/1996 | Regula et al. |
| 5,569,490 A | 10/1996 | Imura et al. |
| 5,605,713 A | 2/1997 | Boltong |
| 5,607,685 A | 3/1997 | Cimbollek et al. |
| 5,652,016 A | 7/1997 | Imura et al. |
| 5,683,461 A | 11/1997 | Lee et al. |
| 5,683,496 A | 11/1997 | Ison et al. |
| 5,695,729 A | 12/1997 | Chow et al. |
| 5,697,981 A | 12/1997 | Ison et al. |
| 5,702,449 A | 12/1997 | McKay |
| 5,766,669 A | 6/1998 | Pugh et al. |
| 5,782,971 A | 7/1998 | Constantz et al. |
| 5,814,681 A | 9/1998 | Hino et al. |
| 5,820,632 A | 10/1998 | Constantz et al. |
| 5,846,312 A | 12/1998 | Ison et al. |
| 5,891,448 A | 4/1999 | Chow et al. |
| 5,899,939 A | 5/1999 | Boyce et al. |
| 5,954,867 A | 9/1999 | Chow et al. |
| 5,958,430 A | 9/1999 | Campbell et al. |
| 5,964,932 A | 10/1999 | Ison et al. |
| 5,976,234 A | 11/1999 | Chow et al. |
| 5,993,535 A | 11/1999 | Sawamura et al. |
| 5,997,624 A | 12/1999 | Chow et al. |
| 6,005,162 A | 12/1999 | Constantz |
| 6,013,591 A | 1/2000 | Ying et al. |
| 6,013,853 A | 1/2000 | Athanasiou et al. |
| 6,027,742 A | 2/2000 | Lee et al. |
| 6,077,989 A | 6/2000 | Kandel et al. |
| 6,083,229 A | 7/2000 | Constantz et al. |
| 6,117,456 A | 9/2000 | Lee et al. |
| 6,118,043 A | 9/2000 | Nies et al. |
| 6,123,731 A | 9/2000 | Boyce et al. |
| 6,132,463 A | 10/2000 | Lee et al. |
| 6,162,258 A | 12/2000 | Scarborough et al. |
| 6,277,149 B1 | 8/2001 | Boyle et al. |
| 6,294,041 B1 | 9/2001 | Boyce et al. |
| 6,294,187 B1 | 9/2001 | Boyce et al. |
| 6,323,146 B1 | 11/2001 | Pugh et al. |
| 6,325,987 B1 | 12/2001 | Sapieszko et al. |
| 6,325,992 B1 | 12/2001 | Chow et al. |
| 6,332,779 B1 | 12/2001 | Boyce et al. |
| 6,340,648 B1 | 1/2002 | Imura et al. |
| 6,379,453 B1 | 4/2002 | Lin et al. |
| 6,440,444 B2 | 8/2002 | Boyce et al. |
| 6,458,162 B1 | 10/2002 | Koblish et al. |
| 6,478,825 B1 | 11/2002 | Winterbottom et al. |
| 6,495,156 B2 | 12/2002 | Wenz et al. |
| 6,530,955 B2 | 3/2003 | Boyle et al. |
| 6,533,821 B1 | 3/2003 | Lally |
| 6,547,866 B1 | 4/2003 | Edwards et al. |
| 6,569,489 B1 | 5/2003 | Li |
| 6,585,992 B2 | 7/2003 | Pugh et al. |
| 6,616,742 B2 | 9/2003 | Lin et al. |
| 6,648,960 B1 | 11/2003 | Lin et al. |
| 6,670,293 B2 | 12/2003 | Edwards et al. |
| 6,696,073 B2 | 2/2004 | Boyce et al. |
| 6,719,989 B1 | 4/2004 | Matsushima et al. |
| 6,730,129 B1 | 5/2004 | Hall |
| 6,752,831 B2 | 6/2004 | Sybert et al. |
| 6,793,725 B2 | 9/2004 | Chow et al. |
| 6,808,561 B2 | 10/2004 | Genge et al. |
| 6,808,585 B2 | 10/2004 | Boyce et al. |
| 6,840,995 B2 | 1/2005 | Lin et al. |
| 6,929,692 B2 | 8/2005 | Tas |
| 6,953,594 B2 | 10/2005 | Lee et al. |
| 6,955,716 B2 | 10/2005 | Xu et al. |
| 6,960,249 B2 | 11/2005 | Lin et al. |
| 6,994,726 B2 | 2/2006 | Lin et al. |
| 2002/0019635 A1 | 2/2002 | Wenstrom, Jr. et al. |
| 2002/0073894 A1 | 6/2002 | Genge et al. |
| 2002/0137812 A1 | 9/2002 | Chow et al. |
| 2002/0169066 A1 | 11/2002 | Cassidy et al. |
| 2003/0019396 A1 | 1/2003 | Edwards et al. |
| 2003/0021824 A1 | 1/2003 | Lacout et al. |
| 2003/0031698 A1 | 2/2003 | Roeder et al. |
| 2003/0055512 A1 | 3/2003 | Genin et al. |
| 2003/0074081 A1 | 4/2003 | Ayers et al. |
| 2003/0078317 A1 | 4/2003 | Lin et al. |
| 2003/0120351 A1 | 6/2003 | Tofighi |
| 2003/0121450 A1 | 7/2003 | Lin et al. |
| 2003/0167093 A1 | 9/2003 | Xu et al. |
| 2003/0216777 A1 | 11/2003 | Tien et al. |
| 2004/0003757 A1 | 1/2004 | Chern Lin et al. |
| 2004/0022825 A1 | 2/2004 | Lagow |
| 2004/0031420 A1 | 2/2004 | Lin et al. |
| 2004/0076685 A1 | 4/2004 | Tas |
| 2004/0137032 A1 | 7/2004 | Wang |
| 2004/0175320 A1 | 9/2004 | Lin et al. |
| 2004/0180091 A1 | 9/2004 | Lin |
| 2004/0185181 A1 | 9/2004 | Matsumoto |
| 2004/0186481 A1 | 9/2004 | Chern Lin et al. |
| 2005/0029701 A1 | 2/2005 | Lin et al. |
| 2005/0069479 A1 | 3/2005 | Lin et al. |
| 2005/0076813 A1 | 4/2005 | Lin et al. |
| 2005/0101964 A1 | 5/2005 | Lin et al. |
| 2005/0184417 A1 | 8/2005 | Lin et al. |
| 2005/0184418 A1 | 8/2005 | Lin et al. |
| 2005/0186353 A1 | 8/2005 | Lin et al. |
| 2005/0186354 A1 | 8/2005 | Lin et al. |
| 2005/0186449 A1 | 8/2005 | Lin et al. |
| 2005/0263919 A1 | 12/2005 | Lin et al. |
| 2005/0263920 A1 | 12/2005 | Lin et al. |
| 2005/0263921 A1 | 12/2005 | Lin et al. |
| 2005/0263922 A1 | 12/2005 | Lin et al. |
| 2005/0263927 A1 | 12/2005 | Lin et al. |
| 2005/0263928 A1 | 12/2005 | Lin et al. |
| 2005/0263929 A1 | 12/2005 | Lin et al. |
| 2005/0263930 A1 | 12/2005 | Lin et al. |
| 2005/0263931 A1 | 12/2005 | Lin et al. |
| 2005/0267587 A1 | 12/2005 | Lin et al. |
| 2005/0267588 A1 | 12/2005 | Lin et al. |
| 2005/0267589 A1 | 12/2005 | Lin et al. |
| 2005/0267593 A1 | 12/2005 | Lin et al. |
| 2005/0267604 A1 | 12/2005 | Lin et al. |
| 2005/0268820 A1 | 12/2005 | Lin et al. |
| 2005/0268821 A1 | 12/2005 | Lin et al. |
| 2005/0271740 A1 | 12/2005 | Lin et al. |
| 2005/0271741 A1 | 12/2005 | Lin et al. |
| 2005/0271742 A1 | 12/2005 | Lin et al. |
| 2005/0274282 A1 | 12/2005 | Lin et al. |
| 2005/0274286 A1 | 12/2005 | Lin et al. |
| 2005/0274287 A1 | 12/2005 | Lin et al. |
| 2005/0274288 A1 | 12/2005 | Lin et al. |

| 2005/0274289 A1 | 12/2005 | Lin et al. |
| 2005/0279256 A1 | 12/2005 | Lin et al. |
| 2006/0011099 A1 | 1/2006 | Lin et al. |
| 2006/0011100 A1 | 1/2006 | Lin et al. |

FOREIGN PATENT DOCUMENTS

| WO | WO 03/055418 | 7/2003 |

OTHER PUBLICATIONS

Pickel et al., "The Effect of a Chewing Gum Containing Dicalcium Phosphate on Salivary Calcium and Phosphate", Ala. J. Med. Sci. 1965, vol. 2, pp. 286-287.
Matsuya et al., "Effects of pH on the Reactions of Tetracalcium Phosphate and Dicalcium Phosphate", IADR Abstract 1991.
Sugawara et al,, "Formation of Hydroxyapatite in Hydrogels from Tetracalcium Phosphate/Dicalcium Phosphate Mixtures," J. Nihon. Univ. Sch. Dent., 1989, vol. 31, pp. 372-381.
Hong et al., The Periapical Tissue Reactions to a Calcuim Phosphate Cement in the Teeth of Monkeys, J Biomed Mater Res. Apr. 1991, vol. 25(4), pp. 485-498.
DeRijk, et al., "Clinical Evaluation of a Hydroxyapatite Precipitate for the Treatment of Dentinal Hypersensitivity, Biomedical Engineering v. Recent Developments," Proc. of 5th Southern Biomedical Engineering Conference, 1986, pp. 336-339. (Pergamon Press, New York).
Groninger et al. "Evaluation of the Biocompatibility of a New Calcium Phosphate Setting Cement," J. Dent Res. 1984, 63 Abst. No. 270 (4 pages).
Costantino et al., Evaluation of a New Hydroxyapatite Cement: Part III, Cranioplasty ina Cat Model, The Fifth Intl. Symposium on Facial Plastic Reconstructive Surgery of the Head and Neck, Toronto, Canada 1989. (18 pages).
Shindo, et al., "Facial Skeletal Augmentation Using Hydroxyapatite Cement," Arch. Otolaryngol. Head Neck Surg. 1993, vol. 119, pp. 185-190.
Briner et al., "Significance of Enamel Remineralization", J. Dent. Res. 1974, vol. 53, pp. 239-243.
Silverstone, "Remineralization Phenomena", Caries Res. 1977, vol. 11 (Supp. 1), pp. 59-84.
Costantino et al., "Hydroxyapatite Cement—Basic Chemistry and Histologic Properties," Arch. of Otolaryngology—Head & Neck Surgery, 1991, vol. 117, pp. 379-394.
Friedman et al., "Hydroxyapatite Cement II. Obliteration and Reconstruction of the Cat Frontal Sinus," Arch. of Otolaryngology—Heady & Neck Surgery, 1991, vol. 117, pp. 385-389.
Contantino et al., "Experimental Hydroxyapatite Cement Cranioplasty," Plastic and Reconstructive Surgery, 1992, vol. 90, No. 2, pp. 174-185.
Miyazaki et al., "An Infrared Spectroscopic Study of Cement Formation of Polymeric Calcium Phosphate Cement," Jour of the Jap. Scoiety for Dent Mats & Devices, 1992, vol. II, No. 2. (8 pages).
Driskell et al., "Development of Ceramic and Ceramic Composite Devices for Maxillofacial Applications", J. Biomed. Mat. Res. 1972, vol. 6, pp. 345-361.
Hiatt et al., "Root Preparation I. Obduration of Dentinal Tubules in Treatment of Root Hypersensitivity", J. Periodontal, 1972, vol. 43, pp. 373-380.
Patel et al., "Solubility of $CaHPO_4$ $2H_2O$ in the Quaternary System $Ca(OH)_2$—$H_3PO_4$—NaCl—$H_2O$ at 25° C.," J. Res. Nat. Bur. Stands. 1974, vol. 78A, pp. 675-681.
Salyer et al., "Porous Hydroxyapatite as an Onlay Bone-Graft Substitute for Maxillofacial Surgery," Presented at the 54th Annual Scientific Meeting of the American Society of Plastic and Reconstructive Surgeons, Kansas City, Missouri, 1985, pp. 236-244.
Kenney et al., "The Use of a Porous Hydroxyapatite Implant in Periodontal Defects," J. Periodontal, 1988, pp. 67-72.
Zide et al., "Hydroxyapatite Cranioplasty Directly Over Dura," J. Oral Maxillofac Surg. 1987, vol. 45, pp. 481-486.
Waite, et al., "Zygomatic Augmentation with Hydroxyapatite," J. Oral Maxillofac Surg 1986, pp. 349-352.
Verwoerd, et al. "Porous Hydroxyapatite-perchondrium Graft in Cricoid Reconstruction, Acta Otolaryngol" 1987, vol. 103, pp. 496-502.
Grote, "Tympanoplasty With Calcium Phosphate," Arch Otolaryngology 1984, vol. 110, pp. 197-199.
Kent et al., "Alveolar Ridge Augmentation Using Nonresorbable Hydroxyapatite with or without Autogenous Cancellous Bone," J. Oral Maxillofac Surg 1983, vol. 41, pp. 629-642.
Piecuch, "Augmentation of the Atrophic Edentulous Ridge with Porus Replamineform Hydroxyapatite (Interpore-200)", Dental Clinics of North America 1985, vol. 30(2), pp. 291-305.
Misch, "Maxillary Sinus Augmentation for Endosteal Implants: Organized Alternative Treatment Plans," Int J Oral Implant 1987, vol. 4(2), pp. 49-58.
Chohayeb, A. A. et al., "Evaluation of Calcium Phosphate as a Root Canal Sealer-Filler Material," J Endod 1987, vol. 13, pp. 384-386.
Brown et al., "Crystallography of Tetracalcium Phosphate," Journal of Research of the National Bureau of Standards. A. Physics and Chemistry. 1965, vol. 69A, pp. 547-551.
Sanin et al. "Particle Size Effects on pH and Strength of Calcium Phosphate Cement," IADR Abstract 1991.
Chow et al., "X-ray Diffraction and Electron Microscopic Characterization of Calcium of Calcium Phosphate Cement Setting Reactions," IADR Abstract, 1987. (1 page).
Block et al. "Correction of Vertical Orbital Dystopia with a Hydroxyapatite Orbital Floor Graft," J. Oral Maxillofac Surg 1988, vol. 46, pp. 420-425.
Brown, "Solubilities of Phosphates and Other Sparingly Soluble Compounds", Environmental Phosphorous Handbook 1973, pp. 203-239. (John Wiley & Sons, New York).
Gregory et al., "Solubility of $CaHPO_4$ $2H_2O$ in the System $Ca(OH)_2$—$H_3PO_4$—$H_2O$ at 5, 15, 25, and 37.5° C.," J. Res. Nat. Bur. Stand. 1970, vol. 74A, pp. 461-475.
Gregory et al., "Solubility of β—$Ca_3(PO_4)_2$ in the System $Ca(OH)_2$—$H_3PO_4$—$H_2O$ at 5, 15, 25, and 37° C.," J. Res. Nat. Bur. Stand. 1974, vol. 78A, pp. 667-674.
McDowell et al., "Solubility of β—$Ca_5(PO_4)_3$ OH in the System $Ca(OH)_2$—$H_3PO_4$—$H_2O$ at 5, 15, 25, and 37° C.," J. Res. Nat. Bur. Stand. 1977, vol. 91A, pp. 273-281.
McDowell et al., "Solubility Study of Calcium Hydrogen Phosphate. Ion Pair Formation," Inorg. Chem. 1971, vol. 10, pp. 1638-1643.
Moreno et al., "Stability of Dicalcium Phosphate Dihydrate in Aqueous Solutions and Solubility of Octocalcium Phosphate," Soil Sci. Soc. Am. Proc. 1960, vol. 21, pp. 99-102.
Chow et al, "Self Setting Calcium Phosphate Cements," Mat. Res. Soc. Symp. Proc. pp. 3-23.
Miyazaki et al., "Chemical Change of Hardened PCA/CPC Cements in Various Storing Solutions", The Journal of the Japanese Soc. for Dental Materials and Devices, 1992, vol. 11, No. 2.
Fukase et al, "Thermal Conductivity of Calcuim Phosphate Cement", IADR Abstract, 1990 (1 page).
Sugawara et al. "Biocompatibility and Osteoconductivity of Calicum Phosphate Cement", IADR Abstract 1990. (1 page).
Miyazaki et al., "Polymeric Calcium Phosphate Cements" IADR Abstract 1990. (1 page).
Link et al., "Composite of Calcium Phosphate Cement and Genetically Engineered Protein Bioadhesive," IADR Abstract 1991. (1 page).
Matsuya et al., "Effects of pH on the Reactions of Tetracalcium Phosphate and Dicalcium Phosphate", IADR Abstract 1991. (1 page).
Chow, "Development of Self-Setting Calcium Phosphate Cements", Journal of The Ceramic Society of Japan, 1991, vol. 99 [10], pp. 954-964.
Brown et al., A New Calcium Phosphate, Water Setting Cement, Cements Research Progress 1986, P. W. Brown, Ed., Westerville, Ohio: American Ceramic Society, 1988, pp. 352-379.

Sugawara et al., "Evaluation of Calcium Phosphate as a Root Canal Sealer-Filler Material"IADR/AADR Abstract, 1987, (3 pages).

Sugawara et al., "In Vitro Evaluation of the Sealing Ability of a Calcium Phosphate Cement When Used as a Root Canal Sealer Filler," J. Endodontics, 1989, vol. 16, pp. 162-165.

Chow, "Calcium Phosphate Materials: Reactor Response" Adv Dent Res 1988, vol. 2(1), pp. 181-184.

Fukase et al., "Setting Reactions and Compressive Strengths of Calcium Phosphate Cements", J Dent Res 1990, vol. 69(12), pp. 1852-1856.

Miyazaki et al., "Chemical Change of Hardened PCA/CPC Cements in Various Storing Solutions", The Journal of the Japanese Soc. for Dental Materials and Devices, 1992, vol. 11, No. 2, pp. 48-64.

Combined ISR/Written Opinion relating to Int'l Appl. No. PCT/US04/36951, Mailed Jan. 4, 2006.

IPER relating to Int'l Appl. No. PCT/US2005/004025, Mailed Mar. 26, 2006.

* cited by examiner

INJECTABLE CALCIUM PHOSPHATE CEMENTS AND THE PREPARATION AND USE THEREOF

RELATED APPLICATION

This is a continuation application and claims the benefit of priority under 35 USC § 120 to U.S. patent application Ser. No. 10/414,582 filed on Apr. 16, 2003, which is a continuation-in-part of U.S. patent application Ser. No. 09/615,384, filed Jul. 13, 2000, now abandoned, which is a continuation-in-part of U.S. patent application Ser. No. 09/351,912, filed Jul. 14, 1999, now U.S. Pat. No. 6,379,453. The disclosure of the prior application is considered part of and is incorporated by reference in the disclosure of this application.

BACKGROUND OF THE INVENTION

1. Field of the Invention

The present invention is related to a calcium phosphate cement, and in particular a fast-setting calcium phosphate cement, for use in dental and bone prosthesis.

2. Description of the Related Art

A calcium phosphate cement (abbreviated as CPC) has been widely used as an implant or filling material in dental and bone prosthesis, and its technical details can be found in many patents, for examples U.S. Pat. Nos. 4,959,104; 5,092,888; 5,180,426; 5,262,166; 5,336,264; 5,525,148; 5,053,212; 5,149,368; 5,342,441; 5,503,164; 5,542,973; 5,545,254; 5,695,729 and 5,814,681. In general, the prior art calcium phosphate cements suffer one or more drawbacks as follows: 1) additives having a relatively poor bioactivity being required; 2) a complicated preparation process; 3) an undesired setting time or working time of CPC, which are difficult to be adjusted; 4) not capable of being set to a desired shape in water, blood or body fluid; and 5) poor initial strength after setting of the CPC.

SUMMARY OF THE INVENTION

An object of the present invention is to provide a calcium phosphate cement.

Another object of the present invention is to provide a calcium phosphate cement comprising particles having whiskers or fine crystals on surfaces of the particles. Still another object of the present invention is to provide a process for preparing a calcium phosphate cement.

A further object of the present invention is to provide a method of treating a bone or a tooth having a defect in a patient by using a calcium phosphate cement.

In order to accomplish the above objects of the present invention a calcium phosphate cement prepared in accordance with the present invention comprises calcium phosphate particles having a diameter of 0.05 to 100 microns, wherein said calcium phosphate particles on their surfaces have whiskers or fine crystals having a width ranging from 1 to 100 nm and a length ranging from 1 to 1000 nm. By adjusting the diameter of the calcium phosphate particles, the width and/or the length of the whiskers or fine crystals, the inventors of the present invention are able to adjust the working time and/or the setting time of the calcium phosphate cement of the present invention to conform to requirements for various purposes. Moreover, the calcium phosphate cement of the present invention is fast-setting, and is non-dispersive in water or an aqueous solution.

DETAILED DESCRIPTION OF THE PREFERRED EMBODIMENTS

Figure 1:
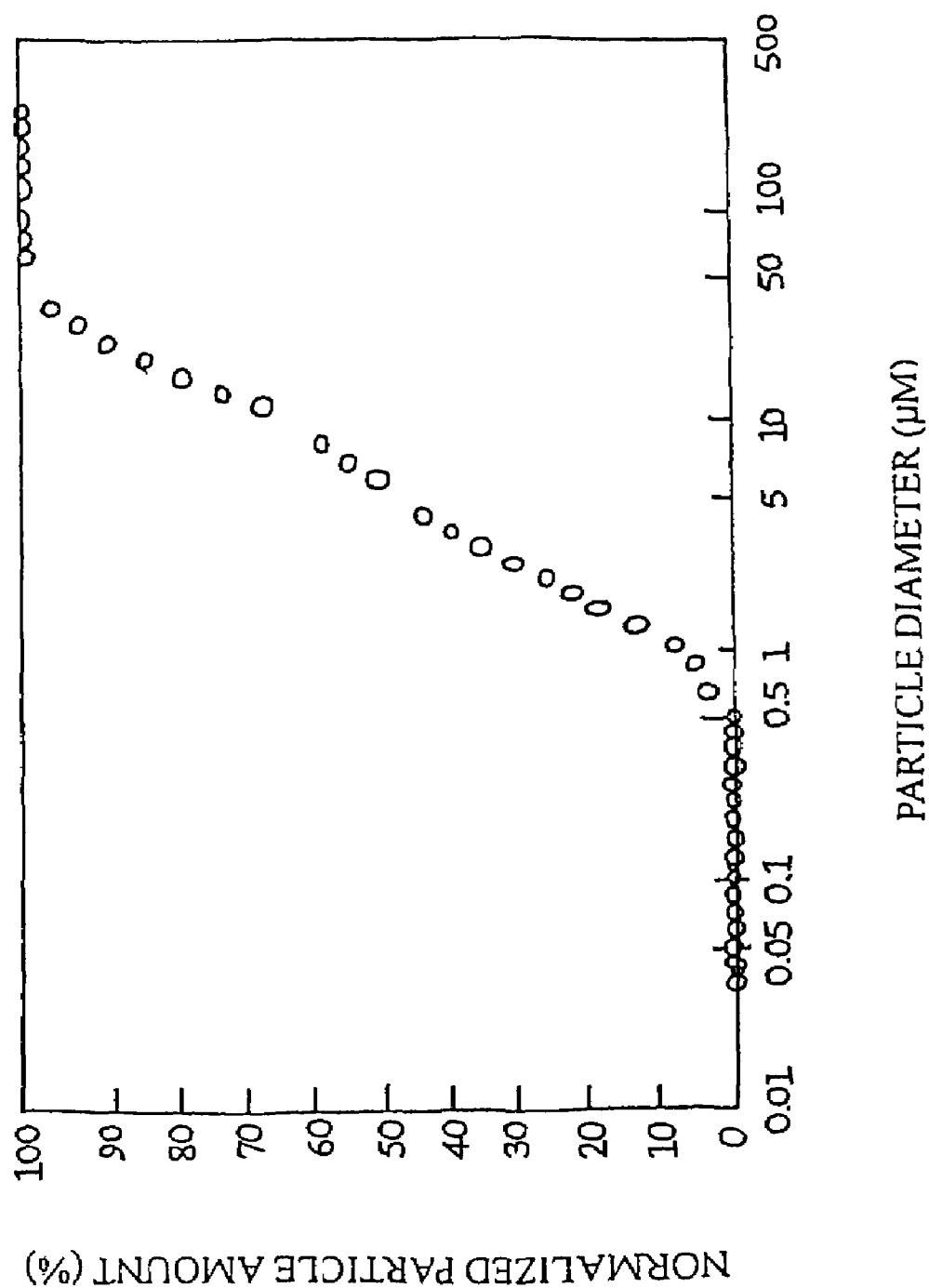
FIG. 1 is a normalized particle amount (%) versus particle diameter (pm) plot showing a particle diameter distribution of a calcium phosphate cement (CPC) prepared in accordance with the following Example 6 of the present invention.

A suitable process for preparing the calcium phosphate cement of the present invention comprises mixing a calcium phosphate powder or small pieces of calcium phosphate with a wetting agent, and controlling growth of whiskers or fine crystals on surfaces of said calcium phosphate powder or small pieces of calcium phosphate by an controlling treatment.

Suitable calcium phosphates for use as the calcium phosphate powder or small pieces of calcium phosphate in the present invention can be any known calcium phosphates such as calcium dihydrogen phosphate, tetracalcium phosphate, calcium dihydrogen phosphate hydrate, acid calcium pyrophosphate, anhydrous calcium hydrogen phosphate, calcium hydrogen phosphate hydrate, calcium pyrophosphate, calcium triphosphate, calcium polyphosphate, calcium metaphosphate, anhydrous tricalcium phosphate, tricalcium phosphate hydrate, apatite, hydroxyapatite, a mixture thereof and an adduct thereof. Moreover, the shape of the calcium phosphate powder and the shape of the small pieces of calcium phosphate are not limited, which can be spherical or irregular; and the crystal structure thereof can be single crystal, polycrystal, mixed crystals, semi-crystal, or amorphous.

The process for preparing the calcium phosphate cement preferably further comprises grinding the resulting product from the controlling treatment to form calcium phosphate particles having a diameter of 0.05 to 100 microns, wherein said whiskers or fine crystals have a width ranging from 1 to 100 nm and a length ranging from 1 to 1000 nm.

Said controlling treatment is a vacuuming treatment, an organic solvent treatment, a microwave treatment, a heating treatment, or any other treatments which can control growth of whiskers or fine crystals on surfaces of said calcium phosphate powder or small pieces of calcium phosphate.

Said wetting agent is used to wet the calcium phosphate powder or small pieces of calcium phosphate, and preferably is a diluted aqueous solution containing phosphoric acid or phosphate. The amount of said wetting agent mixed with the calcium phosphate powder or small pieces of calcium phosphate, in general, should be enough to wet substantially all the calcium phosphate powder or small pieces of calcium phosphate. However, it is not necessarily the case when said controlling treatment is the organic solvent treatment, where a water miscible organic. solvent is added to the mixture of said wetting agent and said calcium phosphate powder or small pieces of calcium phosphate to form a paste for a subsequent processing step.

Preferably, said wetting agent is a diluted aqueous solution containing more than 20 ppm of phosphoric acid or phosphate, more preferably more than 50 ppm, and most preferably more than 100 ppm of phosphoric acid or phosphate.

Preferably, the process for preparing the calcium phosphate cement of the present invention comprises soaking said calcium phosphate powder or said small pieces of calcium phosphate with said diluted aqueous solution containing more than 100 ppm of phosphoric acid or phosphate, and carrying out (a) said heating treatment comprising drying the resulting soaked calcium phosphate powder or soaked small pieces of calcium phosphate at a temperature higher than 45° C.; (b) said vacuuming treatment comprising drying the resulting soaked calcium phosphate powder or soaked small pieces of calcium phosphate under vacuum; or (c) said microwave treatment comprising drying the resulting soaked calcium phosphate powder or soaked small pieces of calcium phosphate by microwave heating. More preferably, the resulting soaked calcium phosphate powder or soaked small pieces of calcium phosphate is well mixed to form a uniform mixture prior to being subjected to treatment (a), (b) or (c).

Alternatively, the process for preparing the calcium phosphate cement of the present invention comprises mixing said calcium phosphate powder or said small pieces of calcium phosphate with said diluted aqueous solution containing more than 100 ppm of phosphoric acid or phosphate, and carrying out said organic solvent treatment comprising mixing the mixture of said wetting agent and said calcium phosphate powder or small pieces of calcium phosphate with a water miscible organic solvent, and drying the resulting mixture under vacuum. Preferably, said organic solvent treatment is carried out while stirring, and more preferably, the mixture of said diluted aqueous solution containing more than 100 ppm of phosphoric acid or phosphate and said calcium phosphate powder or small pieces of calcium phosphate is well mixed prior to being subjected to said organic solvent treatment.

Preferably, said calcium phosphate particles of the calcium phosphate cement of the present invention have a diameter of 0.2 to 80 microns, and more preferably 0.5 to 50 microns.

The width of a whisker means an average value of lateral cross-sectional diameters of the whisker, and the width of a fine crystal means an average value of the first 30% of the diameters of the fine crystal, which are shorter than the other 70% thereof. The length of a fine crystal means an average value of the last 30% of the diameters of the fine crystal, which are longer than the other 70% thereof.

Preferably, said whiskers or fine crystals have a width ranging from 2 to 70 nm and a length ranging from 5 to 800 nm, and more preferably a length ranging from 10 to 700 nm.

Preferably, said calcium phosphate particles have a molar ratio of calcium to phosphate ranging from 0.5 to 2.5, more preferably 0.8 to 2.3, and most preferably 1.0 to 2.2.

The calcium phosphate cement of the present invention is biocompatible and a paste made therefrom is non-dispersive in water, which has a working time from several minutes to hours and a setting time from a few minutes to hours. Consequently, the calcium phosphate cement of the present invention is extremely suitable for use as an implant or filling material in dental or bone prosthesis, where the paste must contact water, blood or body fluid. Particularly, the paste made from the calcium phosphate cement of the present invention is able to be directly injected into a bone defect or cavity as an implant or filling material.

The present invention also discloses a method of treating a born or a tooth having a defect in a patient, comprising mixing the calcium phosphate cement of the present invention and a hardening-promoter-containing aqueous solution to form a paste, and a) injecting said paste into a bone defect or cavity of said patient or b) shaping said paste and implanting the resulting shaped paste into a bone defect or cavity of said patient.

In the method of the present invention, said calcium phosphate cement may further comprise a growth factor, a bone morphology protein or a pharmaceutical carrier, or said hardening-promoter-containing aqueous solution further comprises a growth factor, a bone morphology protein or a pharmaceutical carrier.

Said hardening-promoter-containing aqueous solution can be an aqueous solution comprising any known compounds or compositions which enable the solidification of calcium phosphate, for examples phosphates, calcium salts, and fluorides. That is said hardening-promoter-containing aqueous solution may be an aqueous solution comprising phosphate ions, calcium ions, fluorine ions, or phosphate ions together with fluorine ions as a hardening promoter.

The content of said hardening promoter in said hardening-promoter-containing aqueous solution has no special limitation, but preferably ranges from 1 mM to 3 M, and more preferably from 10 mM to 1 M.

The mixing ratio of the calcium phosphate cement of the present invention and said hardening-promoter-containing aqueous solution is not restricted to any particular ranges; however, the amount of said hardening-promoter-containing aqueous solution mixed should be sufficient to provide substantial wetting of the calcium phosphate cement of the present invention. It should be noted that more water can be supplied in-situ from saliva or body fluid, when the paste is injected or implanted into the bone defect or cavity. Further, the content of said hardening promoter in said hardening-promoter-containing aqueous solution should be adjusted to a higher level corresponding to a less amount of said hardening-promoter-containing aqueous solution being mixed.

EXAMPLE 1

Heating Treatment 5 g of $Ca(H_2PO_4)_2 \cdot H_2O$ powder and 1.6 ml of 25 mM phosphoric acid aqueous solution were mixed, and stirred for one minute. The resulting mixture was placed into an oven at 50° C. for 15 minutes, and the resulting dried mixture was mechanically ground for 20 minutes to fine particles after being removed from the oven. 1 g of the fine particles and 0.4 ml of phosphate aqueous solution (1.0 M, pH=6.0) were mixed to form a paste, which was tested every 30 seconds to determine the working time and the setting time. The setting time is the time required when a 1 mm diameter pin with a load of ¼ pounds can be inserted only 1 mm deep into the surface of the paste. The working time is the time after which the paste is too viscous to be stirred. The working time of the paste of this example is 30 minutes and the setting time thereof is one hour.

The paste was placed in a relatively large amount of deionized water immediately following the formation thereof, and it was observed that the paste was non-dispersive in deionized water.

EXAMPLE 2

Vacuuming Treatment 5 g of $CaHPO_4$ (DCPA) powder and 1.2 ml of 25 mM phosphoric acid aqueous solution were mixed, and stirred for one minute. The resulting mixture was placed in a vacuum environment of −100 Pa for 30 minutes, and the resulting dried mixture was mechanically ground for 20 minutes to fine particles. 1 g of the fine particles and 0.4 ml of phosphate aqueous solution (1.0 M, pH=6.0) were mixed to form a paste, which was tested every 30 seconds to determine the working time and the setting time. The working time of the paste of this example is 20.5 minutes and the setting time thereof is 24 minutes.

The paste was placed in a relatively large amount of deionized water immediately following the formation thereof, and it was observed that the paste was non-dispersive in deionized water.

EXAMPLE 3

Organic Solvent Treatment 5 g of $CaHPO_4$ (DCPA) powder and 1.6 ml of 25 mM phosphoric acid aqueous solution were mixed, and stirred for one minute. To the resulting mixture 1.6 ml of acetone was added while stirring to form a paste followed by placing in a vacuum environment of −100 Pa for one hour, and the resulting dried mixture was mechanically ground for 20 minutes to fine particles. 1 g of the fine particles and 0.4 ml of phosphate aqueous solution (1.0 M, pH=6.0) were mixed to form a paste, which was tested every 30 seconds to determine the working time and the setting time. The working time of the paste of this example is 20.0 minutes and the setting time thereof is 22.0 minutes.

The paste was placed in a relatively large amount of deionized water immediately following the formation thereof, and it was observed that the paste was non-dispersive in deionized water.

EXAMPLE 4

Microwave Treatment 3 g of a mixed powder of $CaHPO_4$ (DCPA) and $Ca_4(PO_4)_2O$ (TTCP) in 1:1 molar ratio was mixed with 2.0 ml of 25 mM phosphoric acid aqueous solution, and the mixture was stirred for five minutes. The resulting mixture was placed in a microwave oven where it was heated under low power for five minutes. The resulting dried mixture was mechanically ground for 20 minutes to fine particles. 1 g of the fine particles and 0.42 ml of phosphate aqueous solution (1.0 M, pH=6.0) were mixed to form a paste, which was tested every 30 seconds to determine the working time and the setting time. The working time of the paste of this example is 2.0 minutes and the setting time thereof is 4.0 minutes.

The paste was placed in a relatively large amount of deionized water immediately following the formation thereof, and it was observed that the paste was non-dispersive in deionized water.

EXAMPLE 5

Heating Treatment 5 g of a mixed powder of DCPA and TTCP in 1:1 molar ratio was mixed with 1.6 ml of 25 mM phosphoric acid aqueous solution, and the mixture was stirred for one minute. The resulting mixture was placed in a high temperature oven at 500° C. for five minutes. The resulting dried mixture was mechanically ground for 20 minutes to fine particles. 1 g of the fine particles and 0.4 ml of phosphate aqueous solution (1.0 M, pH=6.0) were mixed to form a paste, which was tested every 30 seconds to determine the working time and the setting time. The working time of the paste of this example is 1.5 minutes and the setting time thereof is 2.5 minutes.

The paste was placed in a relatively large amount of deionized water immediately following the formation thereof, and it was observed that the paste was non-dispersive in deionized water.

EXAMPLE 6

Heating Treatment 5 g of a mixed powder of DCPA and TTCP in 1:1 molar ratio was mixed with 1.6 ml of 25 mM phosphoric acid aqueous solution, and the mixture was stirred for one minute. The resulting mixture was placed in a high temperature oven at 1000° C. for one minute. The resulting dried mixture was mechanically ground for 20 minutes to fine particles. 1 g of the fine particles and 0.4 ml of phosphate aqueous solution (1.0 M, pH=6.0) were mixed to form a paste, which was tested every 30 seconds to determine the working time and the setting time. The working time of the paste of this example is 31 minutes and the setting time thereof is 35 minutes.

EXAMPLES 7-11

The procedures of Example 1 were repeated except that the $Ca(H_2PO_4)_2 \cdot H_2O$ powder was replaced by a mixed powder of DCPA and TTCP in 1:1 molar ratio and the 25 mM phosphoric acid aqueous solution was replaced by a diluted phosphoric acid aqueous solution having a pH of 1.96. The heating treatments were carried out with conditions listed in Table 1. The performance is also listed in Table 1.

CONTROL EXAMPLE 1

1 g of a mixed powder of DCPA and TTCP in 1:1 mole and 0.4 ml of a diluted phosphoric acid aqueous solution having a pH of 1.96 were mixed to form a paste, which was tested every 30 seconds to determine the working time and the setting time. The paste of this example can not set within hours. The performance is listed in Table 1.

EXAMPLE 12

The procedures of Example 2 were repeated except that the DCPA powder was replaced by a mixed powder of DCPA and TTCP in 1:1 molar ratio and the 25 mM phosphoric acid aqueous solution was replaced by a diluted phosphoric acid aqueous solution having a pH of 1.96. The performance is listed in Table 1.

EXAMPLE 13

The procedures of Example 3 were repeated except that the DCPA powder was replaced by a mixed powder of DCPA and TTCP in 1:1 molar ratio and the 25 mM phosphoric acid aqueous solution was replaced by a diluted phosphoric acid aqueous solution having a pH of 1.96. The performance is listed in Table 1.

EXAMPLE 14

The procedures of Example 4 were repeated except that the 25 mM phosphoric acid aqueous solution was replaced by a diluted phosphoric acid aqueous solution having a pH of 1.96. The performance is listed in Table 1.

TABLE 1

|  | Controlling treatment | Setting/working time (min) | Dispersive in Water |
|---|---|---|---|
| Control Ex. 1 | — | — | Yes |
| Ex. 7 | Heating, 50° C. | 11.5/6.5 | No |
| Ex. 8 | Heating, 100° C. | 13.5/8.0 | No |
| Ex. 9 | Heating, 150° C. | 8.5/8.0 | No |
| Ex. 10 | Heating, 500° C. | 2.5/1.5 | No |
| Ex. 11 | Heating, 1000° C. | 35/31 | No |
| Ex. 12 | Vacuuming | 14.5/11.5 | No |
| Ex. 13 | Organic solvent | 17.5/16.5 | No |
| Ex. 14 | Microwave | 3.5/2.5 | No |

Figure 6A:
FIGS. 6a to 6c are photographs showing a CPC paste of the present invention injected into water via a syringe at 3, 10 and 30 seconds after the CPC paste being formed in accordance with the following Example 7.
Figure 6B:
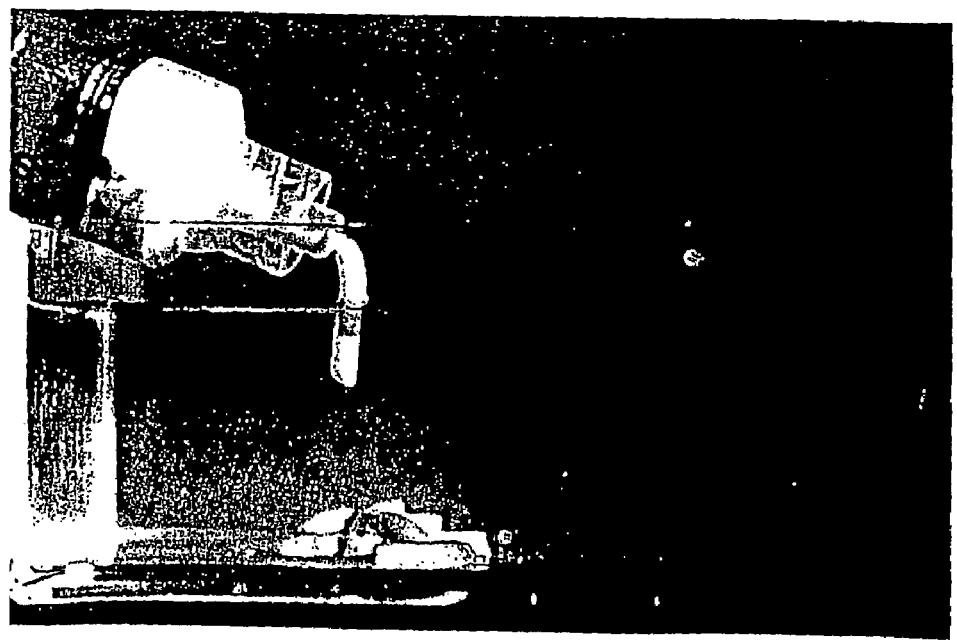
Figure 6C:
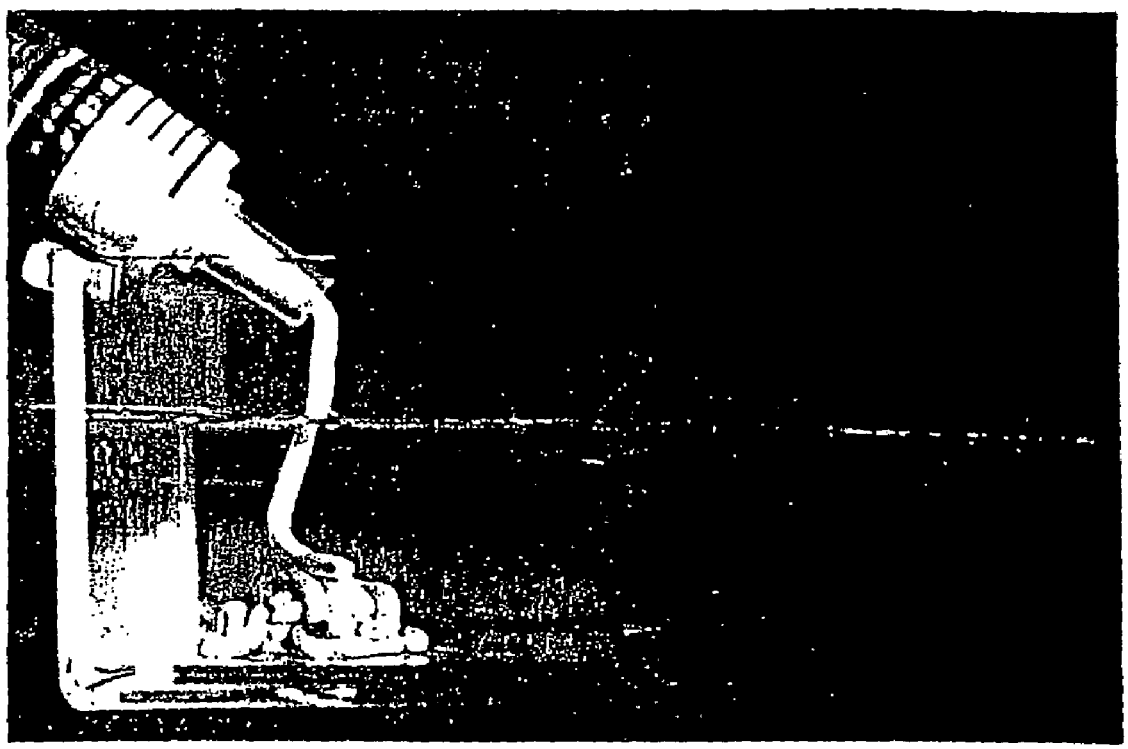

The pastes prepared in Control Example 1 and Example 7 were injected into water via a syringe at 3, 10 and 30 seconds after the paste being formed. The results are shown in FIGS. 5a to 5c and FIGS. 6a to 6c, respectively. It can be seen from FIGS. 5a to 5b that the paste prepared in Control Example 1 is dispersive in water. On the contrary, the paste prepared in Example 7 is non-dispersive as shown in FIGS. 6a to 6c.

Figure 7A:
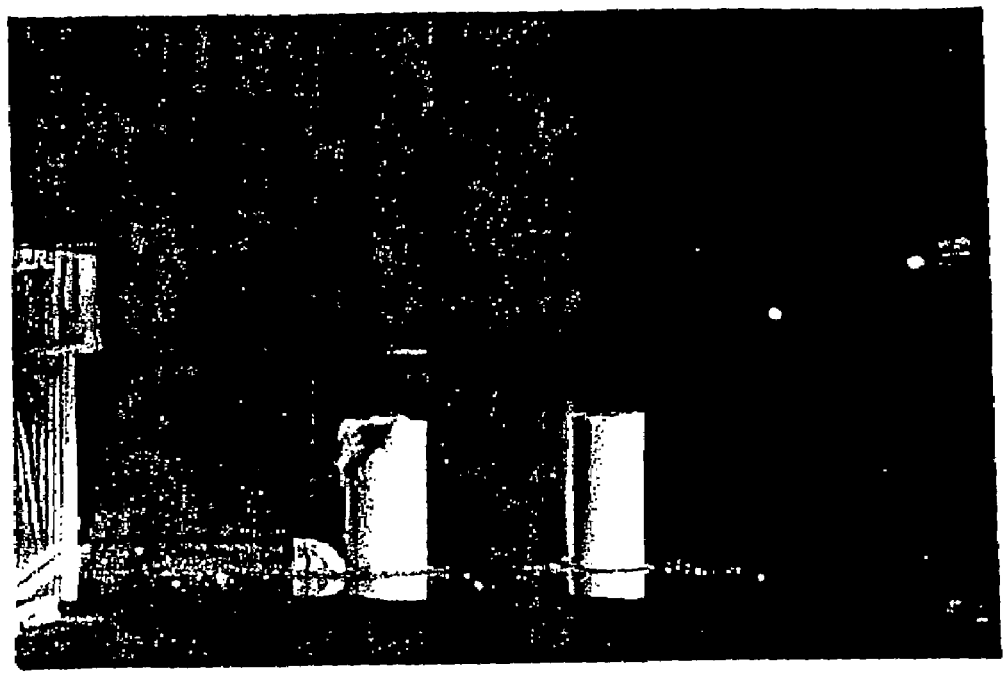
FIGS. 7a to 7c are photographs showing two cylinders prepared by separately molding a conventional CPC paste and a CPC paste of the present invention prepared in the following Example 7, which were taken at 5, 20 and 60 seconds after the two cylinders being immersed in the water.
Figure 7B:
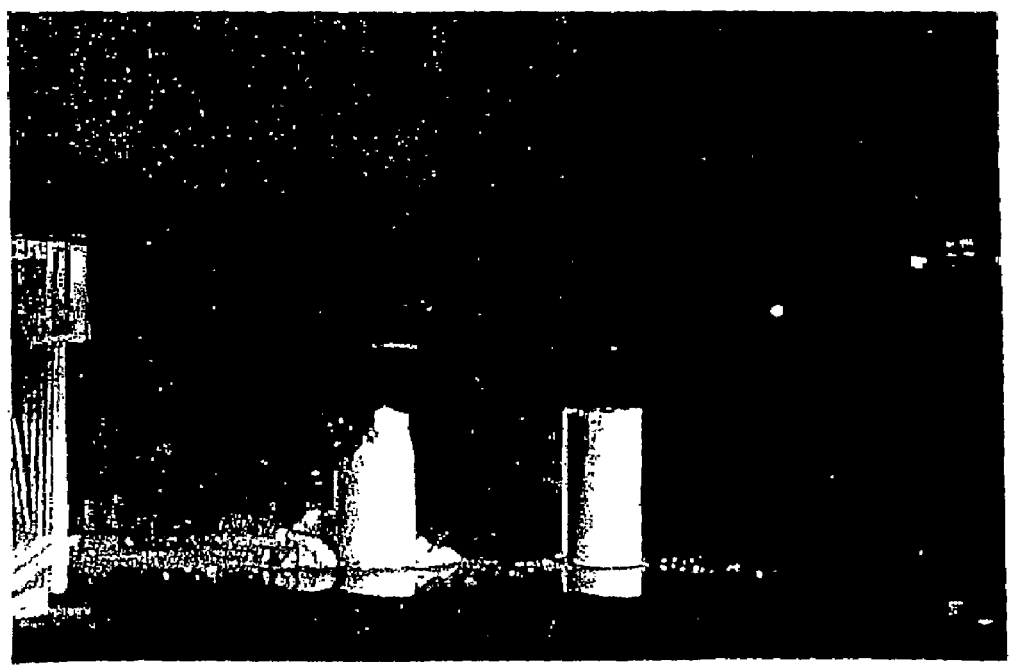
Figure 7C:
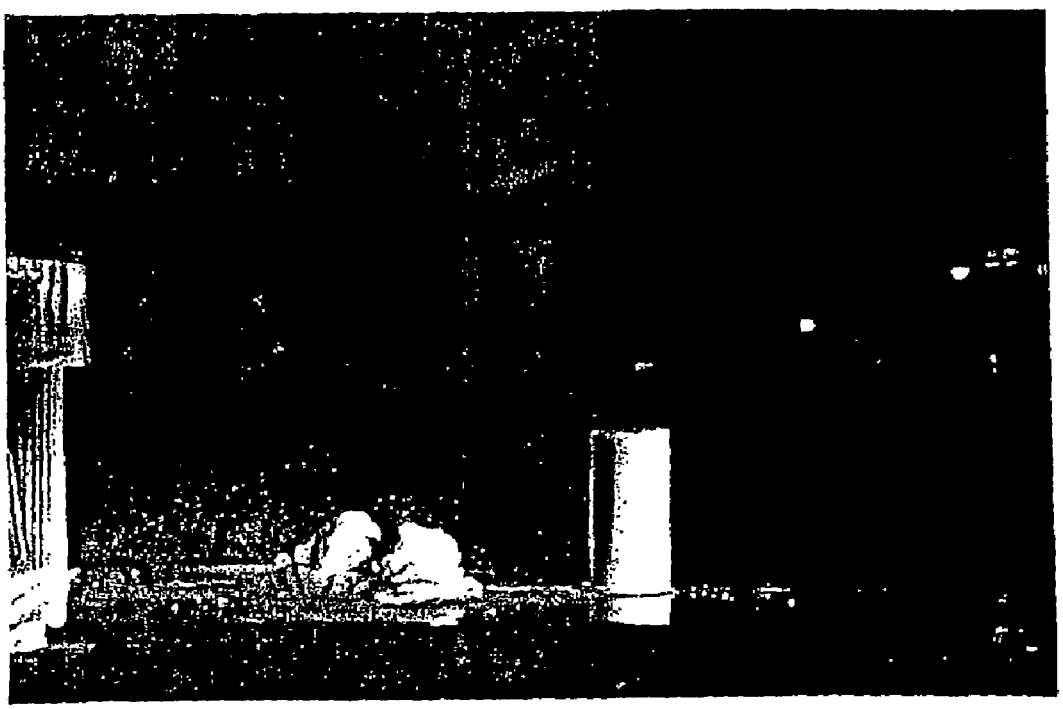

Two cylinders were prepared by separately molding the pastes prepared in Control Example 1 and Example 7, and were then placed in water. FIGS. 7a to 7c show the pictures taken at 5, 20 and 60 seconds after the cylinders being immersed in the water, from which it can be seen that the left cylinder made from the paste prepared in Control Example 1 collapses, while the right cylinder made form the paste prepared in Example 7 remains almost intact.

It can be concluded from the results shown in FIGS. 5a to 7c that the paste prepared from the calcium phosphate cement of the present invention can be directly injected or implanted after being molded into a block into a cavity in a deformed tooth or bone.

Figure 8:
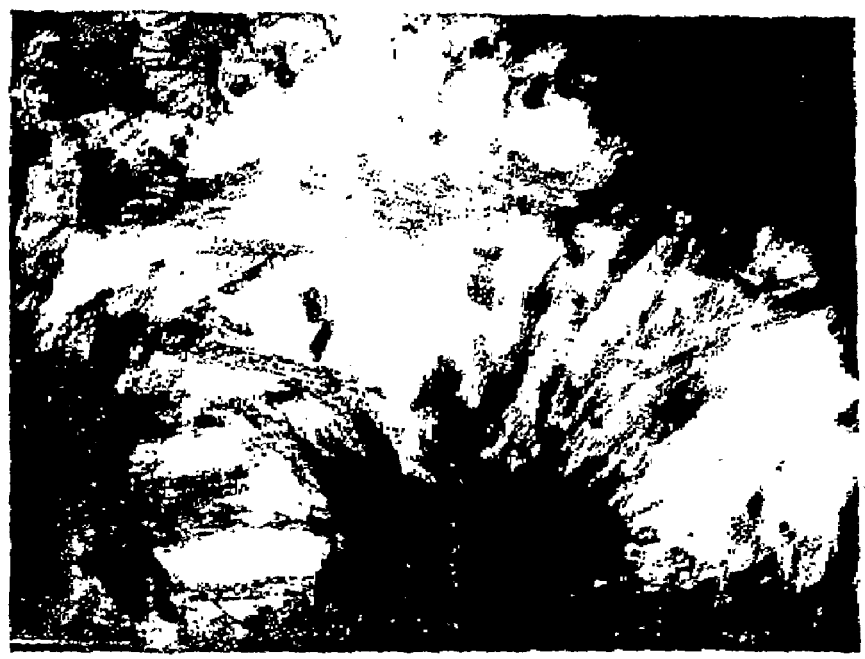
FIG. 8 is a TEM micrograph showing the calcium phosphate cement of the present invention prepared in the following Example 7.
Figure 9:
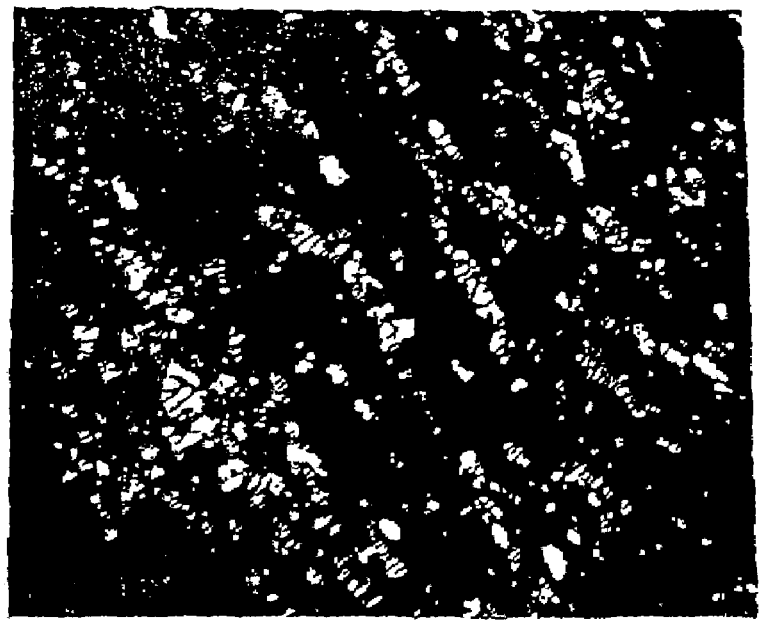
FIG. 9 is a TEM micrograph showing the calcium phosphate cement of the present invention prepared in the following Example 7.

Two samples of the calcium phosphate cement prepared in Example 7 were observed by transmission electron microscopy (TEM), and the two TEM pictures shown in FIGS. 8 and 9 indicate that there are whiskers on surfaces of calcium phosphate particles having different diameters of the calcium phosphate cement.

Figure 2:
FIG. 2 is a scanning electron microscopy (SEM) micrograph of the calcium phosphate cement prepared in accordance with Example 6 of the present invention.
Figure 3:
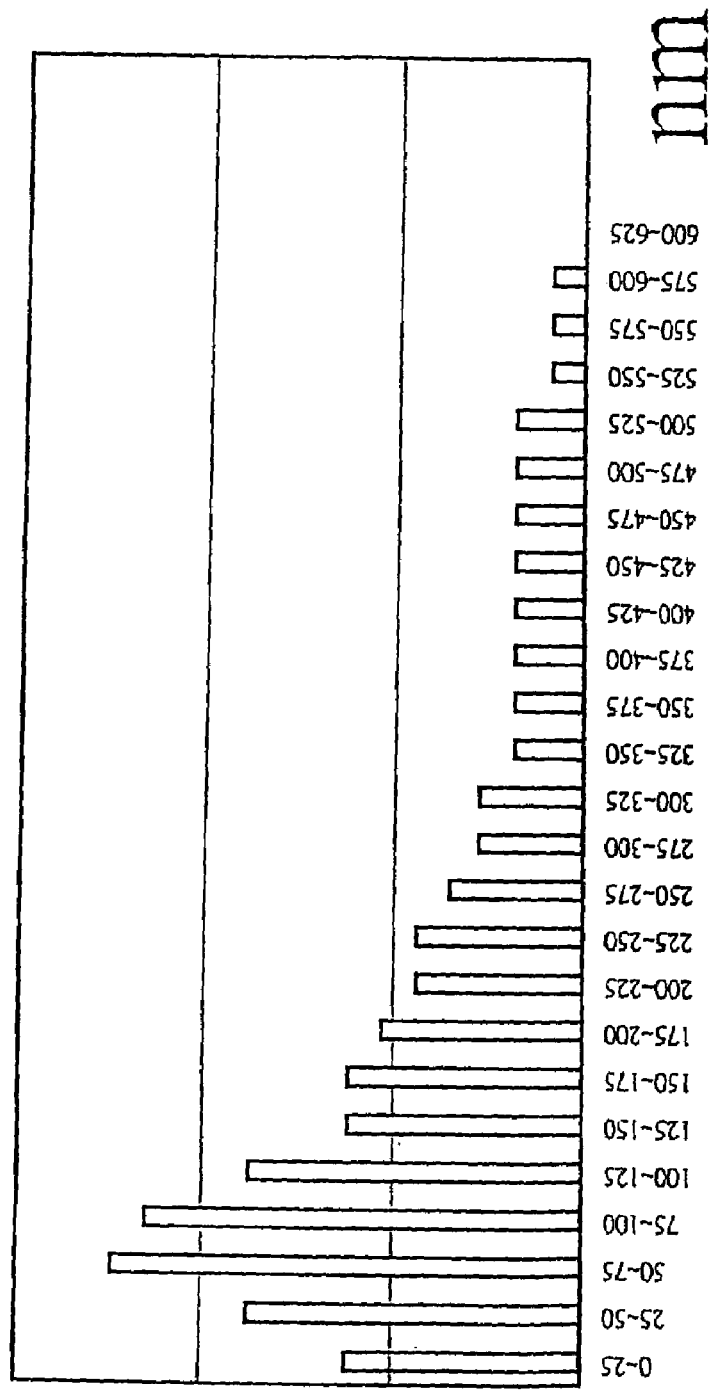
FIGS. 3 and 4 show the distributions of the lengths and the widths of the whiskers or fine crystals on surfaces of the calcium phosphate particles prepared in the following Example 6 of the present invention, respectively, which are determined directly from transmission electron microscopy (TEM).
Figure 4:
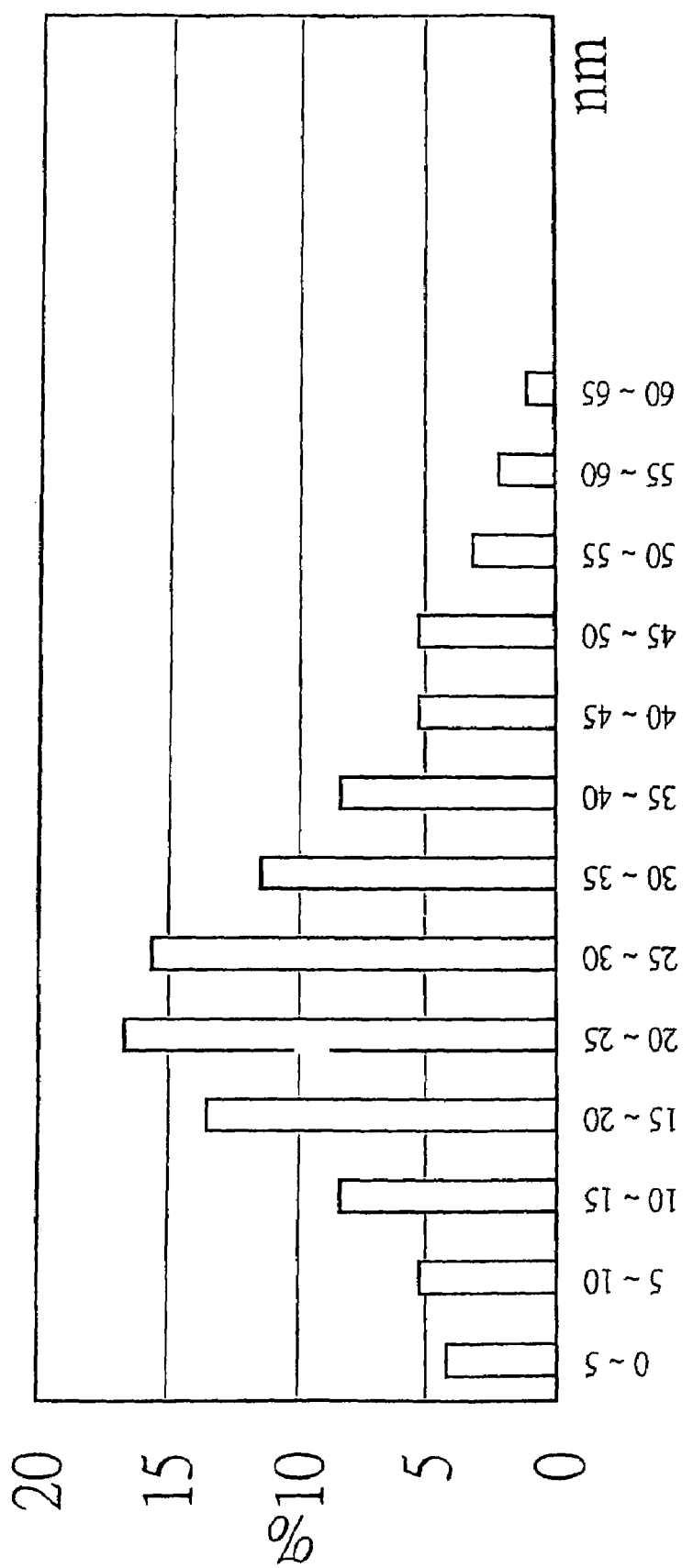
Figure 5A:
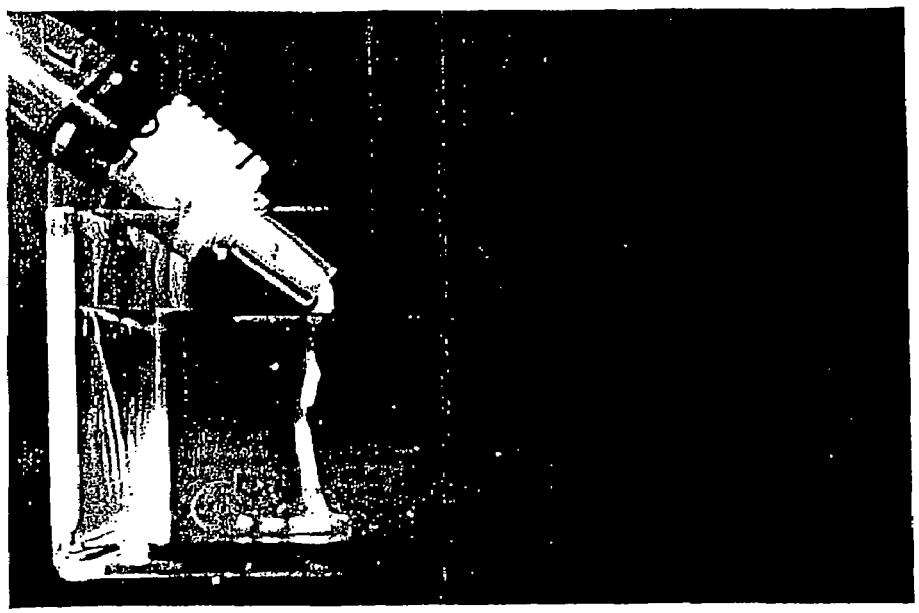
FIGS. 5a to 5c are photographs showing a conventional CPC paste injected into water via a syringe at 3, 10 and 30 seconds after the conventional CPC paste being formed.
Figure 5B:
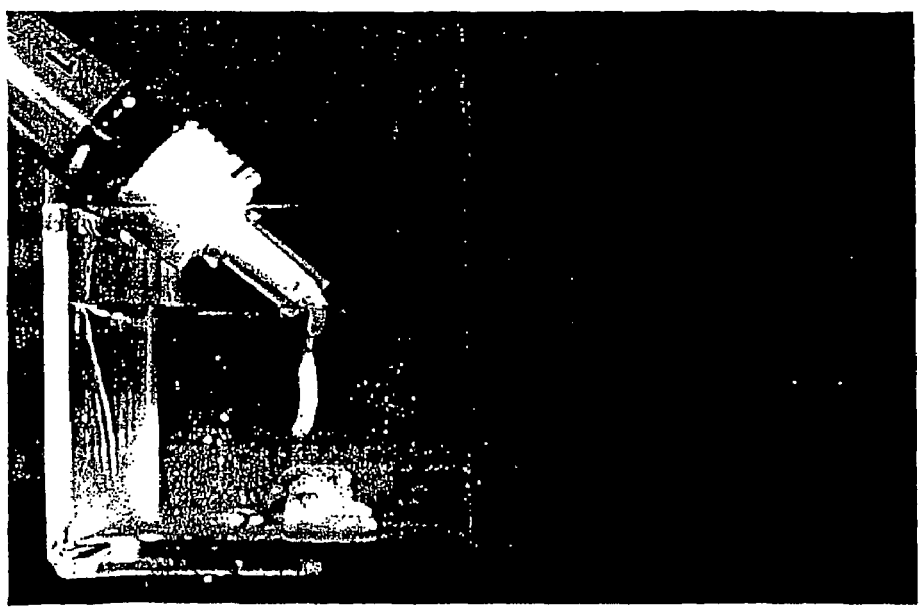
Figure 5C:

The calcium phosphate cement prepared in Example 6 has a particle diameter distribution shown in FIG. 1, which was determined by using particle size analyzer (Sald-2001, Shimadzu Co., Japan). The curve in FIG. 1 indicates that the particle diameters of the calcium phosphate cement prepared in Example 6 range from about 0.47 microns to 93.49 microns. FIG. 2 shows a scanning electron microscopy (SEM) micrograph of the calcium phosphate cement prepared in Example 6. Moreover, the lengths and the widths of the whiskers or fine crystals on surfaces of the calcium phosphate particles prepared in Example 6 were determined directly from TEM (JXA-840, JEOL Co., Japan), and the results are shown in FIGS. 3 and 4, respectively. As shown in FIGS. 3 and 4, the lengths and widths of the of the whiskers or fine crystals on surfaces of the calcium phosphate particles prepared in Example 6 range from 1 to 625 nm and 1 to 65 nm, respectively.

EXAMPLES 15-19

The procedures of Example 7 were repeated by using the calcium phosphate powders and the wetting solutions listed in Table 2. The performance is also listed in Table 2.

TABLE 2

|  | Calcium phosphate powder* | Wetting solution | Heating treatment | Setting/working time (min) | Dispersive in water |
|---|---|---|---|---|---|
| Ex. 15 | TCP | Acetic acid | Yes | 10/6.5 | No |
| Control Ex. 2 | TCP | — | No | — | Yes |
| Ex. 16 | TCP | Acetic acid | Yes | 12.5/8.5 | No |
| Control Ex. 3 | TCP | — | No | — | Yes |
| Ex. 17 | TTCP + DCPA | Phosphoric acid | Yes | 11/18 | No |
| Control Ex. 4 | TTCP + DCPA | — | No | — | Yes |
| Ex. 18 | TTCP + DCPA + TCP | Phosphoric acid | Yes | — | No |
| Control Ex. 5 | TTCP + DCPA + TCP | — | No | — | Yes |

TABLE 2-continued

| | Calcium phosphate powder* | Wetting solution | Heating treatment | Setting/working time (min) | Dispersive in water |
|---|---|---|---|---|---|
| Ex. 19 | DCPA + TCP | Phosphoric acid | Yes | 29/24 | No |
| Control Ex. 6 | DCPA + TCP | — | No | — | Yes |

*TCP is anhydrous tricalcium phosphate.
TTCP + DCPA is a mixed powder of TTCP and DCPA in 1:1 molar ratio.
TTCP + DCPA + TCP is a mixed powder of TTCP + DCPA and TCP in 1:1 weight ratio.
DCPA + TCP is a mixed powder of DCPA and TCP in 1:2 molar ratio.
DCPA + TCP is a mixed powder of DCPA and TCP in 1:2 molar ratio.

CONTROL EXAMPLES 2-6

The procedures of Control Example 1 were repeated by using the calcium phosphate powders and the wetting solutions listed in Table 2. The performance is also listed in Table 2.

EXAMPLES 20-31

The procedures of Example 7 were repeated by using the wetting solutions having different pH values listed in Table 3. The performance is also listed in Table 3.

CONTROL EXAMPLES 7-14

The procedures of Control Example 1 were repeated by using the wetting solutions having different pH values listed in Table 3. The performance is also listed in Table 3.

TABLE 3

| | Wetting solution | pH | Heating treatment | Dispersive in water |
|---|---|---|---|---|
| Ex. 20 | Phosphoric acid | 0.56 | Yes | No |
| Control Ex. 7 | — | — | No | Yes |
| Ex. 21 | Phosphoric acid | 1.03 | Yes | No |
| Ex. 22 | Phosphoric acid | 1.17 | Yes | No |
| Ex. 23 | Phosphoric acid | 1.22 | Yes | No |
| Ex. 24 | Phosphoric acid | 1.32 | Yes | No |
| Ex. 25 | Phosphoric acid | 2.0 | Yes | No |
| Control Ex. 8 | — | — | No | Yes |
| Ex. 26 | Acetic acid + sodium carbonate | 7.0 | Yes | No |
| Control Ex. 9 | — | — | No | Yes |
| Ex. 27 | Sodium hydroxide | 9.5 | Yes | No |
| Control Ex. 10 | — | — | No | Yes |
| Ex. 28 | Sodium hydroxide | 12.55 | Yes | No |
| Control Ex. 11 | — | — | No | Yes |
| Ex. 29 | Acetic acid | 1.96 | Yes | No |
| Control Ex. 12 | — | — | No | Yes |
| Ex. 30 | Ethanol | — | Yes | No |
| Control Ex. 13 | — | — | No | Yes |
| Ex. 31 | Deionized water | 7.0 | Yes | No |
| Control Ex. 14 | — | — | No | Yes |

What is claimed is:

1. A method of forming calcium phosphate cement particles with calcium phosphate crystals on the surface of the particles comprising:
    forming a mixture by contacting calcium phosphate particles with an acidic wetting agent, wherein the calcium phosphate particles comprise tetracalcium phosphate and dicalcium phosphate anhydrous;
    subjecting the mixture to one or more controlling treatments, wherein at least one of the controlling treatments substantially removes the wetting solution from the mixture, and wherein the controlling treatment is chosen such that the treatment causes the growth of fine crystals or whiskers on the surface of at least a portion of the calcium phosphate particles; and
    reducing the size of the calcium phosphate particles such that the calcium phosphate particles have an average diameter ranging from 0.05 microns to 100 microns.

2. The method of claim 1, wherein the calcium phosphate particles are contacted with the wetting agent for 1 minute to 5 minutes.

3. The method of claim 1, wherein the wetting agent is an aqueous phosphoric acid solution.

4. The method of claim 1, wherein the wetting agent is acetic acid.

5. The method of claim 1, wherein the whiskers have a length ranging from 10 microns to 700 nm.

6. The method of claim 1, wherein the at least one controlling treatment is a vacuuming treatment.

7. The method of claim 1, wherein the controlling treatment is selected from the list consisting of a vacuuming treatment, a heating treatment, a microwave treatment and an organic solvent treatment.

8. The method of claim 7, wherein the controlling treatment is an organic solvent treatment.

9. The method of claim 7, wherein the controlling treatment is a microwave treatment.

10. The method of claim 7, wherein the controlling treatment is a heating treatment.

11. The method of claim 10, wherein the mixture is heated to a temperature of greater than 45° C.

* * * * *